United States Patent [19]
Jaynes et al.

[11] Patent Number: 5,744,445
[45] Date of Patent: Apr. 28, 1998

[54] METHOD OF TREATING PULMONARY DISEASE STATES WITH NON-NATURALLY OCCURING AMPHIPATHIC PEPTIDES

[75] Inventors: Jesse M. Jaynes, Baton Rouge, La.; Gordon R. Julian, Cary, N.C.

[73] Assignee: Demeter Biotechnologies, Ltd., Durham, N.C.

[21] Appl. No.: 457,798

[22] Filed: Jun. 1, 1995

Related U.S. Application Data

[63] Continuation of Ser. No. 39,620, Jun. 4, 1993, abandoned.

[51] Int. Cl.$^6$ .................. A61K 38/00; A61K 38/10; A61K 38/16
[52] U.S. Cl. ................. 514/12; 514/13; 514/14
[58] Field of Search ................. 514/12, 13, 14

[56] References Cited

U.S. PATENT DOCUMENTS

| | | | |
|---|---|---|---|
| 4,355,104 | 10/1982 | Hultmark et al. | 435/70 |
| 4,520,015 | 5/1985 | Hultmark et al. | 514/12 |
| 4,810,777 | 3/1989 | Zasloff | 530/326 |
| 5,186,166 | 2/1993 | Riggs et al. | 128/203.15 |
| 5,254,535 | 10/1993 | Zasloff et al. | 514/12 |

OTHER PUBLICATIONS

MP Search Abstracts of WO 901 2826, Jaywes (Nov. 1990).
Jaynes, J.M., et al, "In Vitro Cytocidal Effect of Lytic Peptides on Several Transformed Mammalian Cell Lines," Peptide Research, 2: 157–160 (1989).
Jaynes, J. M., "Lytic Peptides Portned an Innovative Age in the Management and Treatment of Human Disease", Drug News and Perspectives, 3: 69–78 (1990).
Akerfeldt, et al., "Synthetic Peptides as Models for Ion Channel Proteins," Acc. Chem. Res., 26: 191–197 (1993).
Collins, F.S., "Cystic Fibrosis: Molecular Biology and Therapeutic Implications," Science 256: 774–779 (1992).
Jaynes, J.M., et al, "In Vitro Effect of Novel Lytic Peptides on Plasmodium Falciparium and Trypanosoma Cruzi," Faseb J. 2: 2878–2883 (1988).
Gorecki, M. et al, "Non Cationic Substrates of Trypsin," Biochem. and Biophys. Res. Comm. 29 (2): 189–193 (1967).
Higgins, C. F., et al, Nature 262: 250–255 (1993).
Wong, W.S.D., et al "Pyridine Borane as a Reducing Agent for Proteins," Anal. Biochem. 139: 58–67 (1984).
Reed, W. A. et al, "Enhanced In Vitro Growth of Murine Fibroblast Cells and Preimplantation Embroyos Cultured in Medium Supplemented with an Amphipathic Peptide," Molecular Reproduction and Development 31: 106–113 (1992).
Arrowood, M. J., et al, "Hemolytic Properties of Lytic Peptides Active Against the Sporozites of Cryptospordium Parvium," J. Protozool. 38: 161s–163s (1991).

*Primary Examiner*—Cecilia J. Tsang
*Assistant Examiner*—Bennett Celsa
*Attorney, Agent, or Firm*—Rothwell, Figg, Ernst & Kurz

[57] ABSTRACT

A method of treating pulmonary disease states, e.g., a disease state selected from the group consisting of: cystic fibrosis, neoplasias, bronchogenic cancers, pneumonia, bronchitis, bronchopulmonary viral infections, and bronchopulmonary microbial infections, comprising delivery of an amphipathic non-naturally occurring peptide to an appropriate corporeal site, e.g., pulmonary and/or gastrointestinal loci, to effectively treat such diseases. In a further specific aspect, the invention contemplates a method of treating cystic fibrosis by delivery of lytic, amphipathic non-naturally occurring peptides to pulmonary loci, thereby effecting treatment of bronchopulmonary microbial infections associated with cystic fibrosis through lysis of pathogenic bacteria. Peptides delivered to a gastrointestinal locus preferably are non-lytic, so as not to affect normal gastrointestinal flora, and preferably are chemically modified to confer enhanced proteolytic resistance for an oral method of delivery. Peptides delivered to a pulmonary locus advantageously exhibit lytic activity and do not require chemical modification for proteolytic resistance. The delivery of the peptide to a pulmonary locus may for example be effected by use of a nebulizer device.

20 Claims, No Drawings

METHOD OF TREATING PULMONARY DISEASE STATES WITH NON-NATURALLY OCCURING AMPHIPATHIC PEPTIDES

This is a continuation of application Ser. No. 08/039,620, filed Jun. 4, 1993 now abandoned.

BACKGROUND OF THE INVENTION

1. Field of the Invention

The present invention relates to non-naturally occurring amphipathic peptides and their use in methods of treating pulmonary disease states.

2. Description of Related Art

Naturally occurring amphipathic peptides play an important if not critical role as immunological agents in insects and have some, albeit secondary, defense functions in a range of other animals. The function of these peptides is to destroy prokaryotic and other non-host cells by disrupting the cell membrane and promoting cell lysis. Common features of these naturally occurring amphipathic, lytic peptides include an overall basic charge, a small size (23–39 amino acid residues), and the ability to form amphipathic α-helices. Several types of amphipathic lytic peptides have been identified: cecropins (described in U.S. Pat. Nos. 4,355,104 and 4,520,016 to Hultmark et al.), defensins, sarcotoxins, melittin, and magainins (described in U.S. Pat. No. 4,810,777 to Zasloff). Each of these peptide types is distinguished by sequence and secondary structure characteristics.

Several hypotheses have been suggested for the mechanism of action of the lytic peptides: disruption of the membrane lipid bilayer by the amphipathic α-helix portion of the lytic peptide; lytic peptide formation of ion channels, which results in osmotically induced cytolysis; lytic peptide promotion of protein aggregation, which results in ion channel formation; and lytic peptide-induced release of phospholipids. Whatever the mechanism of lytic peptide-induced membrane damage, an ordered secondary conformation such as an α-amphipathic helix and positive charge density are features that appear to participate in the function of the lytic peptides.

Active analogs of naturally occurring lytic peptides have been produced and tested in vitro against a variety of prokaryotic and eukaryotic cell types (see for example Arrowood, M. J., et al. J. Protozool. 38: 161s [1991]; Jaynes, J. M., et al. FASEB J. 2: 2878 [1988]), including: gram positive and gram negative bacteria, fungi, yeast, envelope viruses, virus-infected eukaryotic cells, and neoplastic or transformed mammalian cells. The results from these studies indicate that many of the synthetic lytic peptide analogs have similar or higher levels of lytic activity for many different types of cells, compared to the naturally occurring forms. In addition, the peptide concentration required to lyse microbial pathogens such as protozoans, yeast, and bacteria does not lyse normal mammalian cells.

The specificity of the lytic action depends upon the sequence and structure of the peptide, the concentration of the peptide, and the type of membrane with which it interacts. Jaynes et al. Peptide Research. 2: 157 (1989) discuss the altered cytoskeletal characteristics of transformed or neoplastic mammalian cells that make them susceptible to lysis by the peptides. In these experiments, normal, human non-transformed cells remained unaffected at a given peptide concentration while transformed cells were lysed; However, when normal cells were treated with the cytoskeletal inhibitors cytochalasin D or colchicine, sensitivity to lysis increased. The experiments show that the action of lytic peptides on normal mammalian cells is limited. This resistance to lysis was most probably due to the well-developed cytoskeletal network of normal cells. In contrast, transformed cell lines which have well-known cytoskeletal deficiencies were sensitive to lysis. Because of differences in the sensitivity to lysis of microbial pathogens (high sensitivity), transformed mammalian cells (high sensitivity), and normal mammalian cells (resistant), amphipathic peptide concentration can be manipulated to effect lysis of one cell type but not another at the same locus.

Synthetic peptide analogs can also act as agents of eukaryotic cell proliferation. Amphipathic peptides that promote lysis of transformed cells will, at lower concentrations, promote cell proliferation in some cell types. This stimulatory activity is thought to depend on the channel-forming capability of the amphipathic peptides, which somehow stimulates nutrient uptake, calcium influx or metabolite release, thereby stimulating cell proliferation (see Jaynes, J. M. Drug News & Perspectives 3: 69 [1990]; and Reed, W. A. et al. Molecular Reproduction and Development 31: 106 [1992]). Thus, at a given concentration, these peptides stimulate or create channels that can be beneficial to the normal mammalian cell in a benign environment where it is not important to exclude toxic compounds.

The synthetic amphipathic peptide analogs typically contain as few as 15 and as many as 40 amino acid residues. A phenylalanine residue is often present at the amino terminus of the protein to provide an aromatic moiety analogous to the tryptophan residue located near the amino terminus of natural cecropins, and a UV-absorbing moiety with which to monitor the purification of the synthetic peptide. The basis for the design of these lytic peptide analogs is that an amphipathic peptide of minimal length and containing overall positive charge density effects lytic activity.

A prominent example of a pulmonary disease is cystic fibrosis (CF), a genetic disorder that is inherited in an autosomal recessive manner and affects children and young adults. The clinical features of CF are dominated by involvement of the respiratory tract, where obstruction of the airways by copious amounts of unusually thick mucus and subsequent infections, especially with *Pseudomonas sp.*, predominate. There is also involvement of the gastrointestinal tract in most patients, including malabsorption and pancreatic insufficiency. The affected tissue in CF is the secretory epithelia, which mediates the transport of water, salt, and other solutes at an interface between the blood and a lumen. CF epithelial cells in the skin, lungs and digestive tract cannot properly transport chloride through their membranes, thereby altering water secretion and mucus production.

The defective gene in this disorder has been recently cloned and is known as CFTR (cystic fibrosis transmembrane conductance regulator). The gene product is a protein that functions as a regulated transport channel for chloride ions. Point mutations and deletions in the CFTR gene result in the expression of a defective chloride ion transport channel in epithelial cells, causing the subsequent deleterious symptoms of CF.

There are numerous manifestations of bronchopulmonary viral and microbial infections. Because of a resurgence in antibiotic-resistant strains, many of these infections are a cause of great concern, for example, tuberculosis caused by drug resistant strains of *Mycobacterium tuberculosis*. Other species that cause diseases such as pneumonia also exhibit increasing drug resistance. Moreover, viral infections cannot be treated with antibiotics, and few satisfactory anti-viral medications are available. A secondary effect of the unusual mucosal environment of the CF lung is bronchopulmonary infection associated with chronic progressive lung disease and episodes of acute exacerbation. Colonization of the airways with *Pseudomonas aeruginosa* and cross-infection with *Pseudomonas cepacia* is a major cause of pulmonary deterioration in CF. Members of the Pseudomonas genus are well-known as opportunistic pathogens that have an innate resistance to most commonly used antibiotics. Accordingly, it would be a significant advance in the art to develop an alternative method of treating these microbial and viral bronchopulmonary infections.

Current management of CF includes chest percussion to improve clearance of infected mucus secretions, administration of antibiotics to treat infection, and vigorous attention to nutritional status. Unfortunately, none of these treatments successfully addresses the cause of the symptoms: the defective chloride ion transport channel. Accordingly, it would be a particularly important advance in the art to develop a means of directly treating the chloride channel defect in CF epithelial cells.

Three new pharmacological approaches are directed towards pulmonary complications, which account for 95% of the mortality from CF. In the first approach, amiloride acts as a sodium channel blocker in epithelial cells and may lead to improved mucus hydration; however, amiloride does not directly affect the chloride channel defect. Knowles, M. R. et al. N. Engl. J. Med. 322: 1189 (1990) teach that aerosolized amiloride in clinical trials leads to a slowing of pulmonary deterioration.

In the second approach, Knowles, M. R. et al. N. Engl. J. Med. 325: 533 (1991) teach that application of ATP/UTP to the apical surface of affected pulmonary epithelial cells results in chloride efflux, apparently through an alternative chloride ion transport channel pathway. These observations suggest that delivery of aerosolized ATP and UTP might be beneficial to patients, however, in vivo studies have not yet been done.

In the third approach, Shak, S., et al. Proc. Natl. Acad. Sci USA 87: 9188 (1990), and Hubbard, R. C. et al. N. Engl. J. Med. 326: 812 (1991), teach that aerosolized DNase can be used to reduce the viscosity of the mucus produced in CF. This treatment, although useful, does not address the underlying cause(s) of hyperviscous mucus production.

Gene transfer approaches can also be used to treat CF affected pulmonary epithelia. Several in vitro studies teach that the normal gene can be transfected into epithelial cells using adenoviral vectors, retroviral vectors, DNA-protein complexes, and liposomes. Higgins C. F. et al Nature 262: 250 (1993) teach that aerosolized liposomes can be used to transfect the CFTR gene into mouse pulmonary epithelia in vivo, and Rosenfeld, M. A. et al Cell 68: 143 (1992) teach that CFTR-containing adenovirus can be used to infect rat pulmonary epithelia in vivo. Although these studies are of utmost importance, the drawbacks to be considered are numerous: toxic overexpression of the gene product; vector safety; host immune reactions to the protein or vector; infectivity of relevant cell types; and level and longevity of gene expression.

A simple, safe, and effective pharmacological approach to the treatment of pulmonary disease states such as CF, bronchogenic cancers, and bronchopulmonary microbial and viral infections would be a significant advance in the art.

Accordingly, it is the object of this invention to provide a method of treating pulmonary disease states by delivery of amphipathic non-naturally occurring peptides to pulmonary loci to effectively treat virally infected cells, microbial pathogens, CF affected cells, and neoplastic or transformed cells through peptide interaction with the cellular membrane.

It is another object of this invention to provide a method of treating CF by delivery of amphipathic non-naturally occurring peptides to gastrointestinal loci to effectively treat defective epithelial cells through peptide interaction with the cellular membrane.

It is yet another object of the invention to provide a method of treating neoplasias and bronchogenic cancers by delivery of amphipathic non-naturally occurring peptides to pulmonary loci to effectively lyse transformed cells through peptide interaction with the cellular membrane.

It is another object of this invention to treat cystic fibrosis by delivery of lytic, amphipathic non-naturally occurring peptides to pulmonary loci, thereby effecting treatment of bronchopulmonary microbial infections associated with CF through lysis of pathogenic bacteria.

It is yet a further object of this invention to treat bronchopulmonary infections caused by pathogenic viruses, pathogenic bacteria and pathogenic protozoans by delivery of lytic, amphipathic non-naturally occurring peptides to pulmonary loci, thereby effecting lysis of pathogenic bacteria and protozoa or the virally infected cells.

Peptides delivered to a gastrointestinal locus are preferably non-lytic, so as not to affect normal gastrointestinal flora, and preferably are chemically modified to confer enhanced proteolytic resistance for an oral method of delivery. Peptides delivered to a pulmonary locus advantageously exhibit lytic activity for antimicrobial action and do not require chemical modification for proteolytic resistance. The delivery of the peptide to a pulmonary locus may, for example, be effected by use of a nebulizer device.

These and other objects and advantages will be more fully apparent from the ensuing disclosure and claims.

SUMMARY OF THE INVENTION

The present invention relates generally to a method of treating pulmonary disease states, comprising in vivo delivery to a corporeal site of an effective amount of a non-naturally occurring amphipathic peptide.

In a specific aspect, the present invention relates to a method of treating pulmonary disease states wherein the disease state is selected from the group consisting of: cystic fibrosis, neoplasias, bronchogenic cancers, pneumonia, bronchitis, bronchopulmonary viral infections, and bronchopulmonary microbial infections, comprising in vivo delivery of an effective amount of a non-naturally occurring amphipathic peptide to a pulmonary or gastrointestinal locus.

The invention relates in a further aspect to a method of treating cystic fibrosis, wherein the cells of the pulmonary and gastrointestinal loci are non-transformed, non-virally infected cells and such a peptide does not have a lytic effect on these cells.

The invention relates in a further aspect to such a method of treating pulmonary disease states such as bronchogenic cancer or bronchopulmonary viral infections, wherein a sub-set of the human cells of the pulmonary locus are transformed or virally infected and such a peptide has a lytic effect on the transformed cells or virally infected cells but not the normal cells.

The invention relates in yet another aspect to a method of treating bronchopulmonary microbial infections in a pulmonary disease state such as cystic fibrosis, comprising introduction to a pulmonary locus of a bioavailable non-naturally occurring amphipathic lytic peptide having lytic effect upon said microbial infections.

The invention relates in another aspect to a bi-modal method of treating cystic fibrosis, comprising concomitant introduction to pulmonary and gastrointestinal loci of an effective amount of a non-naturally occurring amphipathic peptide.

The invention relates in yet a further aspect to such a method of treating cystic fibrosis, wherein the said peptides are chemically modified by methylation on the ε-amino group of lysine residues and the α-amino group of the N-terminal acid and/or by glyoxylation of the guanido group of arginine residues and the α-amino group of the N-terminal acid such that the peptide has enhanced in vivo resistance to proteolytic digestion.

The invention relates in a further aspect to a method of treating bronchopulmonary microbial infections in a pulmonary disease state such as cystic fibrosis, wherein said infections comprise bacterial infections causally associated with at least one bacterium selected from the group consisting of *Pseudomonas aeruginosa, Pseudomonas cepacia Streptococcus pneumoniae, Pneumocystis carinii, Hemophilus influenzae, Klebsiella pneumoniae, Chlamydia pneumoniae*, and *Mycobacterium tuberculosis*.

The term "amphipathic" as used herein refers to the distribution of hydrophobic and hydrophilic amino acid residues along opposing faces of an α-helix structure, which results in one face of the α-helix structure being predominantly hydrophobic and the other face being predominantly hydrophilic. The degree of amphipathy of a peptide can be assessed by plotting the sequential amino acid residues on an Edmunson helical wheel.

The term "peptide" as used herein is intended to be broadly construed as inclusive of polypeptides per se having molecular weights of up to 10,000 daltons, as well as proteins having molecular weights of greater that about 10,000 daltons, wherein the molecular weights are number average molecular weights.

The term "methylated" as used herein means that the specified amino groups have been chemically reacted by a method of reductive alkylation or methylation so that the associated hydrogen atoms are replaced by covalently coupled methyl groups.

The term "glyoxylated" as used herein means that the specified guanido and α-amino groups have been chemically reacted such that each is covalently coupled to a glyoxal group.

As used herein, the term "treating" in reference to a physiological condition or disease state, is intended to be broadly construed as comprehending treatment of an existing condition or disease state, for amelioration thereof, as well as prophylactic treatment for prevention or diminution of the potential severity of such condition or disease state.

DETAILED DESCRIPTION OF THE INVENTION AND PREFERRED EMBODIMENTS THEREOF

The present invention provides a method of treating cystic fibrosis and other pulmonary disease states such as bronchogenic cancer and bronchopulmonary infections that avoids many of the problems associated with current treatments and alternative approaches. The method of the present invention treats the specific CF defect instead of symptoms of the defect, and also treats pathogens that are a secondary effect of the CF defect. Peptides delivered to a gastrointestinal locus preferably are non-lytic, so as not to affect normal gastrointestinal flora, and preferably are proteolytically resistant (due to chemical modification) to accommodate oral delivery thereof. Peptides delivered to a pulmonary locus preferably have lytic activity, thereby lysing pathogenic bacteria, virally infected cells, and transformed cells as well as treating the epithelial cell defect of CF, and do not require chemical modification for proteolytic resistance. The delivery of the peptide to a pulmonary locus may advantageously be effected using a nebulizer device.

The features and advantages of the invention are more fully shown by the following illustrative examples and embodiments, which are not to be limitingly construed as regards the broad scope, utility, and applicability of the invention.

EXAMPLE 1

Representative Lytic Peptides

Set out in Table 1 below as illustrative examples of amphipathic peptide analogs of the present invention are the amino acid sequences of a family of related peptide analogs. The peptides may be synthesized according to conventional methods using a Milligen™ peptide synthesizer. Representative peptides from this group are glyoxylated, methylated, and used in subsequent experimental examples. The three letter amino acid symbols are as follows: Ala, alanine; Arg, arginine; Asp, aspartate; Gly, glycine; Ile, isoleucine; Leu, leucine; Lys, lysine; Phe, phenylalanine; and Val, valine. These amphipathic peptide analogs are designated for ease of reference as SEQ ID NO. 1–38.

TABLE 1

PEPTIDE SEQUENCES

SEQ ID NO: 1

Phe Ala Val Ala Val Lys Ala Val Lys Lys Ala Val Lys Lys Val Lys Lys Ala Val Lys Lys Ala Val Lys Lys Lys Lys
1           5              10             15             20             25

SEQ ID NO: 2

Phe Ala Val Ala Val Lys Ala Val Ala Val Lys Ala Val Lys Lys Val Lys Ala Val Lys Lys Val Lys Lys Ala Val Lys Lys Ala Val
1           5              10             15             20             25

Lys Lys Lys Lys
30

TABLE 1-continued

PEPTIDE SEQUENCES

SEQ ID NO: 3

Phe Ala Val Ala Val Lys Ala Val Ala Val Lys Ala Val Ala Val Lys Ala Val Lys Lys Ala Val Lys Lys Val Lys Lys Ala
1           5                   10                  15                  20                  25
Val Lys Lys Ala Val Lys Lys Lys Lys
    30              35

SEQ ID NO: 4

Phe Ala Val Ala Val Lys Ala Val Lys Lys Ala Val Lys Lys Val Lys Lys Ala Val Lys Lys Ala Val
1           5                   10                  15                  20

SEQ ID NO: 5

Phe Ala Val Ala Val Lys Ala Val Ala Val Lys Ala Val Lys Lys Ala Val Lys Val Lys Lys Ala Val Lys Lys Ala Val
1           5                   10                  15                  20                  25

SEQ ID NO: 6

Phe Ala Val Ala Val Lys Ala Val Ala Val Lys Ala Val Ala Val Lys Ala Val Lys Ala Val Lys Lys Val Lys Lys Ala
1           5                   10                  15                  20                  25
Val Lys Lys Ala Val
    30

SEQ ID NO: 7

Phe Ala Val Gly Leu Arg Ala Ile Lys Arg Ala Leu Lys Lys Leu Arg Arg Gly Val Arg Lys Val Ala Lys Arg Lys Arg
1           5                   10                  15                  20                  25

SEQ ID NO: 8

Phe Ala Val Gly Leu Arg Ala Ile Lys Arg Ala Leu Lys Lys Leu Arg Arg Gly Val Arg Lys Val Ala
1           5                   10                  15                  20

SEQ ID NO: 9

Lys Arg Lys Arg Ala Val Lys Arg Val Gly Arg Arg Leu Lys Lys Leu Ala Arg Lys Ile Ala Arg Leu Gly Val Ala Phe
1           5                   10                  15                  20                  25

SEQ ID NO: 10

Ala Val Lys Arg Val Gly Arg Arg Leu Lys Lys Leu Ala Arg Lys Ile Ala Arg Leu Gly Val Ala Phe
1           5                   10                  15                  20

SEQ ID NO: 11

Phe Ala Val Gly Leu Arg Ala Ile Lys Arg Ala Leu Lys Lys Leu Arg Arg Gly Val Arg Lys Val Ala Lys Arg Lys Arg Lys
1           5                   10                  15                  20                  25
Asp Leu
    30

SEQ ID NO: 12

Phe Ala Val Gly Leu Arg Ala Ile Lys Arg Ala Leu Lys Lys Leu Arg Arg Gly Val Arg Lys Val Ala Lys Asp Leu
1           5                   10                  15                  20                  25

SEQ ID NO: 13

Lys Arg Lys Arg Ala Val Lys Arg Val Gly Arg Arg Leu Lys Lys Leu Ala Arg Lys Ile Ala Arg Leu
1            5                   10                  15                  20
Gly Val Ala Phe Lys Asp Leu
        25          30

SEQ ID NO: 14

Ala Val Lys Arg Val Gly Arg Arg Leu Lys Lys Leu Ala Arg Lys Ile Ala Arg Leu Gly Val Ala Phe Lys Asp Leu
1           5                   10                  15                  20                  25

SEQ ID NO: 15

Lys Lys Lys Lys Phe Val Lys Lys Val Ala Lys Val Lys Lys Val Ala Lys Val Ala Lys Val Ala Lys Val Ala Val
1           5                   10                  15                  20                  25

SEQ ID NO: 16

Lys Lys Lys Lys Phe Val Lys Lys Val Ala Lys Lys Val Lys Lys Val Ala Lys Val Ala Lys Val Ala Val Ala Lys Val
1           5                   10                  15                  20                  25
Ala Val Ala Val
    30

TABLE 1-continued

PEPTIDE SEQUENCES

SEQ ID NO: 17

Lys Lys Lys Lys Phe Val Lys Lys Val Ala Lys Val Lys Val Ala Lys Lys Val Ala Lys Val Ala Val Ala Lys Val
1           5                    10                  15                  20                  25
Ala Val Ala Lys Val Ala Val Ala Val
    30              35

SEQ ID NO: 18

Phe Val Lys Lys Val Ala Lys Lys Val Lys Lys Val Ala Lys Lys Val Ala Lys Val Ala Val
1           5                    10                  15                  20

SEQ ID NO: 19

Phe Val Lys Lys Val Ala Lys Lys Val Lys Lys Val Ala Lys Lys Val Ala Val Ala Lys Val Ala Val Ala Val
1           5                    10                  15                  20                  25

SEQ ID NO: 20

Phe Val Lys Lys Val Ala Lys Lys Val Lys Lys Val Ala Lys Lys Val Ala Val Ala Lys Val Ala Val Ala Lys
1           5                    10                  15                  20                  25
Val Ala Val Ala Val
    30

SEQ ID NO: 21

Lys Lys Lys Lys Phe Val Lys Lys Val Ala Lys Val Ala Lys Lys Val Ala Lys Lys Val Ala Lys Val Ala Lys Lys Val
1           5                    10                  15                  20                  25

SEQ ID NO: 22

Lys Lys Lys Lys Phe Val Lys Lys Val Ala Lys Val Ala Lys Lys Val Ala Lys Lys Val Ala Lys Val Ala Lys Lys Val Ala
1           5                    10                  15                  20                  25
Lys Lys Val Ala
    30

SEQ ID NO: 23

Lys Lys Lys Lys Phe Val Lys Lys Val Ala Lys Val Ala Lys Lys Val Ala Lys Lys Val Ala Lys Val Ala Lys Lys Val Ala
1           5                    10                  15                  20                  25
Lys Lys Val Ala Lys Val Ala Lys Lys
    30              35

SEQ ID NO: 24

Phe Val Lys Lys Val Ala Lys Val Ala Lys Lys Val Ala Lys Val Ala Lys Lys Val Ala Lys Lys Val
1           5                    10                  15                  20

SEQ ID NO: 25

Phe Val Lys Lys Val Ala Lys Val Ala Lys Lys Val Ala Lys Val Ala Lys Lys Val Ala Lys Lys Val Ala Lys Lys Val Ala
1           5                    10                  15                  20                  25

SEQ ID NO: 26

Phe Val Lys Lys Val Ala Lys Val Ala Lys Lys Val Ala Lys Val Ala Lys Lys Val Ala Lys Lys Val Ala Lys Lys Val Ala
1           5                    10                  15                  20                  25
Lys Val Ala Lys Lys
    30

SEQ ID NO: 27

Phe Val Lys Lys Val Ala Lys Val Ala Lys Lys Val Ala Lys Val Ala Lys Lys Val Ala Lys Lys Val Lys Lys Lys Lys
1           5                    10                  15                  20                  25

SEQ ID NO: 28

Phe Val Lys Lys Val Ala Lys Val Ala Lys Lys Val Ala Lys Val Ala Lys Lys Val Ala Lys Lys Val Ala Lys Lys Val Ala
1           5                    10                  15                  20                  25
Lys Lys Lys Lys
    30

SEQ ID NO: 29

Phe Val Lys Lys Val Ala Lys Val Ala Lys Lys Val Ala Lys Val Ala Lys Lys Val Ala Lys Lys Val Ala Lys Lys Val Ala
1           5                    10                  15                  20                  25
Lys Val Ala Lys Lys Lys Lys Lys
    30              35

TABLE 1-continued

PEPTIDE SEQUENCES

SEQ ID NO: 30

Phe Lys Val Lys Ala Lys Val Lys Ala Lys Val Lys Lys Lys Lys Lys
1         5            10            15

SEQ ID NO: 31

Phe Lys Val Lys Ala Lys Val Lys Ala Lys Val Lys Ala Lys Val Lys Ala Lys Lys Lys Lys
1         5            10            15            20

SEQ ID NO: 32

Phe Lys Val Lys Ala Lys Val Lys Ala Lys Val Lys Ala Lys Val Lys Ala Lys Val Lys Ala Lys Val Lys Lys Lys
1         5            10            15            20            25

SEQ ID NO: 33

Phe Lys Val Lys Ala Lys Val Lys Ala Lys Val Lys
1         5            10

SEQ ID NO: 34

Phe Lys Val Lys Ala Lys Val Lys Ala Lys Val Lys Ala Lys Val Lys Ala
1         5            10            15

SEQ ID NO: 35

Phe Lys Val Lys Ala Lys Val Lys Ala Lys Val Lys Ala Lys Val Lys Ala Lys Val
1         5            10            15            20

SEQ ID NO: 36

Lys Lys Lys Lys Phe Lys Val Lys Ala Lys Val Lys Ala Lys Val Lys
1         5            10            15

SEQ ID NO: 37

Lys Lys Lys Lys Phe Lys Val Lys Ala Lys Val Lys Ala Lys Val Lys Ala Lys Val Lys Ala
1         5            10            15            20

SEQ ID NO: 38

Lys Lys Lys Lys Phe Lys Val Lys Ala Lys Val Lys Ala Lys Val Lys Ala Lys Val Lys Ala Lys Val Lys Ala Lys Val
1         5            10            15            20            25

---

Chemical modification of amphipathic peptide analogs offers certain advantages. If the modifications are made in such a way that the peptides retain all or most of their amphipathic characteristics, then the physiologically active peptides have enhanced stability to proteolysis. With enhanced stability, oral delivery of the peptide is advantageously accommodated without excessive loss of activity due to proteolytic digestion.

EXAMPLE 2

Chemical Modification by Methylation

An exemplary and preferred reaction scheme for reductive alkylation of lysine residue ε-amino group and the N-terminal α-amino group is described below.

The preferred method for reductive alkylation uses pyridine borane as the reducing agent. This reagent is one of a class of reducing agents known as amine boranes. Pyridine borane exhibits a slightly higher reducing capacity than sodium cyanoborohydride, another reducing agent that can be used for the reductive alkylation. Pyridine borane drives the reductive alkylation reaction to complete dimethylation with no monomethyl products when excess reagents are used, as demonstrated by Wong, W. S. D., et al. Analytical Biochemistry 139: 58 (1984). While as much as 25% of cyanoborohydride goes to N-cyanomethyl products, lowering its methylation yield, pyridine borane does not appear to be involved in any such secondary reaction. In addition, sodium cyanoborohydride provides the potential hazard of contaminating the product with cyanide, severely limiting its use in therapeutic and in vivo applications. The alkylation reagent may suitably comprise formaldehyde as a methyl group (methylation) precursor. Shown below are the agents of reductive alkylation, formaldehyde and pyridine borane, the substrate, peptidyl lysine, and the chemical formulae of the reaction scheme species.

REACTION SCHEME 1:
DIMETHYLATION OF PEPTIDYL LYSINE

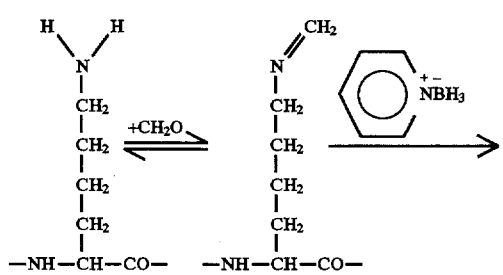

-continued
REACTION SCHEME 1:
DIMETHYLATION OF PEPTIDYL LYSINE

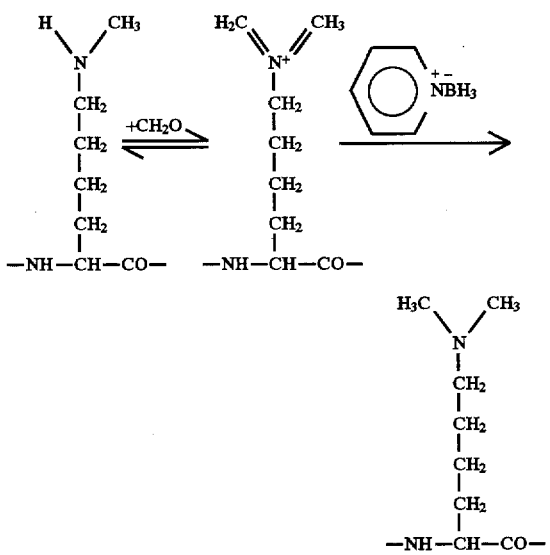

REACTION SCHEME 2:
GLYOXYLATION OF PEPTIDYL ARGININE

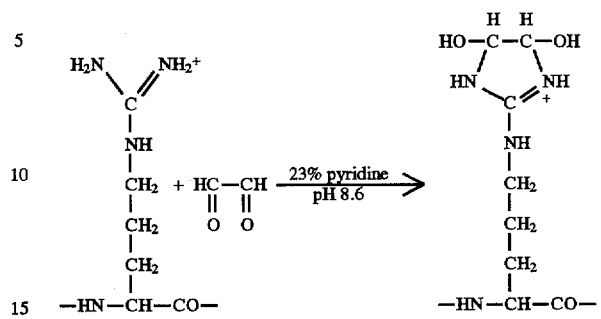

In the reductive alkylation reaction, 20 mg of a representative lysine containing a peptide taken from the group shown in Table 1 was dissolved in 1.6 ml 0.2M HEPES buffer (N-2-hydroxyehylpeperazine-N'-2-ethane sulfonic acid), pH 7.0. While the mixture was stirring, 0.2 ml of 1.2M pyridine borane (0.750 concentrated pyridine borane in 5 ml HPLC grade methanol) was added. Next, 0.2 ml of 0.726M formaldehyde (0.6 ml 37% formaldehyde [HCHO] in 10 ml HEPES pH 7.0 buffer) was added to the mixture. A trace (approximately 1 µl) of 1-octanol was included in the reaction volume to control foaming. The reaction volume was then stirred for 2 hours at room temperature. After 2 hours the reaction mixture was titrated to below pH 3.0 with 0.2M HCL. The reaction mixture was then frozen and lyophilized to reduce volume, and the resulting residue was washed 3 times with anhydrous ether to remove the pyridine borane. The reaction residue was reconstituted to approximately 2.0 ml with 0.1M acetic acid and applied to a 2.4 cm×31 cm G-15-120µ Sephadex™ column to purify the reaction product. After the calibrated front eluted from the column (0.1M acetic acid was the elution reagent), 20 ml of eluate containing the product was collected and the eluate was lyophilized to dryness.

The peptides were stored at −20° C. in the presence of a desiccant as their acetate salt. For use in the following examples they are dissolved in a saline buffer, pH 7.0, at a concentration of 0.1 mg/ml to 10 mg/ml.

EXAMPLE 3

Chemical Modification by Glyoxylation

An exemplary and preferred reaction scheme for glyoxylation of the guanido groups of arginine residues and the N-terminal α-amino acid in a peptide taken from the group set out in Table 1 is described below.

Potential reagents which are capable of modifying the guanido group arginine with glyoxal under mild conditions and do not require an additional reduction reaction are 2,3-butanedione, phenylglyoxal, and glyoxal. The adducts from 2,3-butanedione and phenylglyoxal were judged to be too unstable, and glyoxal was therefore chosen as the preferred reagent for glyoxylation. The agent of glyoxylation, glyoxal, the substrate, peptidyl arginine, and the chemical reaction scheme are described below.

In the glyoxylation reaction, 5 mg of an arginine-containing peptide from the group shown in Table 1 was dissolved in 1.0 ml of 80% pyridine to form a clear solution. To this mixture 2 ml of 0.5M sodium bicarbonate buffer pH 8.0 ($NaHCO_3$—NaOH) was added. Freshly prepared, 30% glyoxal suspension in the 0.5M sodium bicarbonate buffer was added to the reaction volume and the cloudy reaction mixture was stirred at room temperature for three hours. After 20 minutes the solution became mostly clear although progressively yellow-brown during the course of the reaction. The final concentration of the pyridine was 23%. The pyridine, as a representative heterocyclic amine, was essential to the reaction, in order to maintain the glyoxal/peptide mixture in solution. Other water-soluble dielectric solvents such as the heterocyclic amine piperidine were tested and can be used in the place of pyridine.

At the conclusion of the reaction, glacial acetic acid was added drop-wise to bring the pH to 6.0. A two-phase extraction using three parts ether to one part acetone for the organic phase was repeated three times to remove the majority of the glyoxal. The pyridine was not removed to a significant extent. The preparation was dried in a lyophilizer and the crusty residue was rinsed with three parts ether to one part acetone. The residual ether-acetone was removed in vacuo. The cloudy ether-acetone supernatant was centrifuged to recover a precipitate which was pooled with the remaining residue by washing the tube with glacial acetic acid. The residue was dissolved in glacial acetic acid and a small amount of insoluble material was removed by centrifugation. The solution was then applied to a G-15-120 Sephadex™ column (2.4×31 cm) and eluted with 0.1M acetic acid. The recovered fraction were lyophilized to dryness overnight.

The peptides were stored at −20° C. in the presence of a desiccant as their acetate salt. For use in the following examples they were dissolved in a saline buffer, pH 7.0 at a concentration of 0.1 mg/ml to 10 mg/ml.

EXAMPLE 4

In Vitro Lysis of Pathogenic Bacteria

The effect of a lytic peptide (Hecate-1, homologous to SEQ ID NO. 4) was tested against antibiotic-resistant pathogenic bacteria in vitro. In this test, antibiotic-resistant cultures of *Pseudomonas aeruginosa* and *Klebsiella pneumoniae* were obtained from deceased patients. The lytic peptide bioassay was performed as described below.

A flask containing 49 ml of nutrient broth was inoculated with 1 ml of an overnight culture of the test bacteria. The culture was allowed to grow to mid-log phase at 37° C. with shaking (approximately 4 hours). When the cells reached the correct density, the cells were transferred to a sterile tube and centrifuged for 10 minutes at 3000 rpm. The pellet was resuspended in 3 ml of phosphate buffer and centrifuged for 10 minutes at 3000 rpm. The pellet was resuspended once again in sufficient (but measured) volume to calculate the absorbance of the suspension at 600 nm. Using the resulting absorbance and a previously constructed growth curve, the required dilution to achieve a concentration of $10^6$ cells/ml was determined.

One micromole of the test peptide was dissolved in 1.0 ml of 0.01% acetic acid to make a 1 mM solution and serial dilutions were made to give a range of peptide concentrations from 10 µM to 1 mM. The test culture tubes for the bioassay contained 800 µl of phosphate buffer, pH 7.0, 100 µl of cells at $10^6$ cells/ml and 100 µl of peptide solution (10 µM to 1 mM). The final concentration of peptide in the assay was from 1 µM to 100 µM. A reaction system minus peptide was included as a control. The tubes were incubated at 37° C. for one hour.

After the incubation period, for each tube two 1:10 serial dilutions in phosphate buffer were made (three 1:10 serial dilutions for the control culture). 100 µl of each dilution was spread on an agar plate, in duplicate and incubated overnight at 37° C. The following day, the number of colonies on the control plates was counted to determine the starting number of cells in the assay tubes. The number of cells surviving the assay in the presence of peptide was also counted. The results are shown in Table 2.

TABLE 2

LYSIS OF PATHOGENIC BACTERIA WITH LYTIC PEPTIDE

| Species | No. of Independent Isolates Tested | Average Minimal Inhibitory Concentration |
|---|---|---|
| *Pseudomonas aeruginosa* | 1 | 6.5 µM |
| *Klebsiella pneumoniae* | 4 | 9.9 µM |

The results show that a lytic peptide concentration in the range of 1 µm to 100 µM was effective for lysis of antibiotic resistant *Pseudomonas aeruginosa* and *Klebsiella pneumoniae*, most preferably in the range of 5 µM to 50 µM.

In a second experiment, antibiotic-resistant isolates of *Mycobacterium tuberculosis, Streptococcus pneumoniae, Pneumocystis carinii, Hemophilus influenzae, Klebsiella pneumoniae, Chlamydia pneumoniae*, and *Pseudomonas cepacia* are tested in the same bioassay for lytic activity. Peptide concentration in the range of 1 µm to 100 µM is effective for lysis of the tested pathogenic bacteria, most preferably in the range of 5 µM to 50 µM. This concentration of peptide will be compared with the amount required to treat the pulmonary epithelial cells in a non-toxic manner in order to develop an effective combination dose for concurrent treatment of CF and accompanying bronchopulmonary infections, as well as other pulmonary diseases.

EXAMPLE 5

In Vitro Toxicity of Peptide to Epithelial Cells

A lytic peptide and a chemically modified non-lytic peptide selected from the group shown in Table 1 are tested in vitro with normal and cystic fibrosis affected lung and gastrointestinal epithelial cells, and the cells are assayed for survival. Cell culture is performed according to standard protocols (see for example Reed, W. A. et al. Molecular Reproduction and Development 31: 106 [1992]), and the cytotoxicity assay by $^{51}$Cr release is performed as in Jaynes, J. M. et al. Peptide Research 2: 157 (1989). This test shows a range of peptide concentration that is non-toxic for the cells in vitro. The purpose of the experiment is to formulate a range of safe doses of peptide for in vitro and in vivo experiments. Peptide concentration above 100 µM to 500 µM is toxic for the epithelial cells.

EXAMPLE 6

In Vitro Effectiveness of Chloride Conductance in CF Epithelial Cells

A lytic peptide and a chemically modified non-lytic peptide selected from the group shown in Table 1 are tested in vitro for stimulation of chloride efflux with pulmonary and gastrointestinal epithelial cells, using a range of peptide concentration that is non-toxic to the cells as shown by the experiments in Example 5. The peptides used in this experiment are chemically modified and non-lytic, for the gastrointestinal epithelial cells, and non-modified, lytic peptides for the pulmonary epithelial cells.

The rationale for this experiment is based on previous experiments for cell proliferation (see Reed, W. A. et al. Molecular Reproduction and Development 31: 106 [1992]) which showed that for cultures of epithelial cells, application of peptide in the range of 10 µM to 50 µM stimulated cell growth. The hypothesis for the mechanism of cell growth is that the peptide caused the stimulation of alternative channels or the formation of new channels, providing for better passage of nutrients or metabolites. This hypothesis (e.g. channel formation or stimulation) is also suggested as the mechanism for stimulation of chloride efflux in normal and CF epithelial cells. The cells are cultured according to standard protocols as in Example 5, and chloride efflux is measured according to standard protocols.

Peptide concentration in the range of 1 µM to 50 µM is effective for stimulating chloride efflux from pulmonary and gastrointestinal epithelial cells. Combining the results of the pathogenic bacterial lysis experiment, the epithelial cell toxicity experiment, and the stimulation of chloride efflux experiment yields the following conclusion: a peptide concentration corresponding to 1 µM to 50 µM is the preferred range for treatment of CF affected epithelial cells, microbial infections and other disease states in vitro.

EXAMPLE 7

In Vivo Lysis of Pathogenic Bacteria in Infected Mice

The effect of a representative lytic peptide from the group shown in Table 1 is tested in mice that have bronchopulmonary infections of *Mycobacterium tuberculosis, Pseudomonas aeruginosa*, or *Pseudomonas cepacia*. Mice infected with both antibiotic-resistant and non-resistant bacteria are used, and treatment with antibiotics is compared to treatment with a lytic peptide. A concentration of peptide in the range of 10 µg to 25 mg per kg body weight for the recipient per day is the preferred range for treatment. The desired dose is preferably presented as two, three, four, five, six, or more sub-doses administered at appropriate intervals throughout the day. These sub-doses may be administered in unit dosage forms, for example containing from 10 µg to 1000 mg, preferably from 50 µg to 500 mg, and most preferably from 50 µg to 250 mg of active ingredient per unit dosage form.

An advantageous modality of in vivo pulmonary delivery of the peptide is via a liquid nebulizer inhaler device or a dry powder nebulizer inhaler device, depending on the physical state, solubility, and dosage of the peptide. Suitable nebulizers are commercially available under the trademarks "ROTAHALER", "SPINHALER", and "TURBOHALER". Another potentially suitable powder nebulizer apparatus and method of nebulization is disclosed in U.S. Pat. No. 5,186,166 to Riggs et al.

This experiment shows that peptide in the preferred range of 10 µg to 25 mg per kg body weight for the recipient per day is effective for treatment of mice with bronchopulmonary infections.

EXAMPLE 8

In Vivo Test of CF Mice Treated with Peptide at Pulmonary Site

The effect of a representative lytic, non-chemically modified peptide from Table 1 is tested on previously engineered transgenic mice that are homozygous for the CF defect. The peptide is delivered to a pulmonary locus as described in Example 7. A concentration of peptide in the range of 10 µg to 25 mg per kg body weight for the recipient per day is employed as the preferred range for treatment. The desired dose is preferably presented as two, three, four, five, six, or more sub-doses administered at appropriate intervals throughout the day. These sub-doses may be administered in unit dosage forms, for example containing from 10 µg to 1000 mg, preferably from 50 µg to 500 mg, and most preferably from 50 µg to 250 mg of active ingredient per unit dosage form.

The experiment shows that peptide in the preferred range of 10 µg to 25 mg per kg body weight for the recipient per day is effective for treatment of mice with bronchopulmonary infections.

EXAMPLE 9

In Vivo Test of CF Mice Treated with Modified Peptide at Gastrointestinal Site The effect of a representative non-lytic, chemically modified peptide from Table 1 is tested on previously engineered transgenic mice that are homozygous for the CF defect, as described in Example 8. The peptide is orally delivered to the gastrointestinal locus, and the chemical modification (glyoxylation or methylation) of the peptide confers enhanced proteolytic resistance, as described in Examples 2–3. A concentration of peptide in the range of 10 µg to 25 mg per kg body weight for the recipient per day is utilized as a preferred range for treatment. The desired dose is preferably presented as two, three, four, five, six, or more sub-doses administered at appropriate intervals throughout the day. These sub-doses may be administered in unit dosage forms, for example containing from 10 µg to 1000 mg, preferably from 50 µg to 500 mg, and most preferably from 50 µg to 250 mg of active ingredient per unit dosage form.

The experiment shows that peptide in the preferred range of 10 µg to 25 mg per kg body weight for the recipient per day is effective for treatment of mice with gastrointestinal problems due to CF.

Example 4–9 described above, taken together, demonstrate that a non-toxic, effective dose of amphipathic peptide can be used to treat CF affected epithelia at pulmonary and gastrointestinal sites and resulting bronchopulmonary infections concurrently in vivo. In addition, various compounds of the present invention having appertaining therapeutic ability may be usefully employed in the treatment of other pulmonary disease states including: various neoplasias, bronchogenic cancers, pneumonia, bronchitis, bronchopulmonary viral infections, and bronchopulmonary microbial infections.

In general, suitable doses of the peptides for achievement of therapeutic benefit of the pulmonary diseases such as the disease states listed above will be in the range of 1 µg to 100 mg per kg body weight for the recipient per day, preferably in the range of 10 µg to 50 mg per kg body weight for the recipient per day, and most preferably in the range of 10 µg to 25 mg per kg body weight for the recipient per day. The desired dose is preferably presented as two, three, four, five, six, or more sub-doses administered at appropriate intervals throughout the day. These sub-doses may be administered in unit dosage forms, for example containing from 10 µg to 1000 mg, preferably from 50 µg to 500 mg, and most preferably from 50 µg to 250 mg of active ingredient per unit dosage form.

The mode of administration and dosage forms will of course affect the therapeutic amounts of the peptides which are desirable and efficacious for the treatment. For example, the peptide may be orally administered in a tablet or liquid form or it may be nebulized through the use of a powder or liquid nebulizer inhaler device.

The present invention also contemplates pharmaceutical formulations for human medical use, which comprise as one of the active agents therapeutic amounts of the peptides of Table 1 above as well as other physiologically active compounds. These formulations may for example include as additional components nebulizable compounds such as Survanta® TA pulmonary surfactant (Burroughs Wellcome Co.), Mucomist™ mucolytic agent (Mead-Johnson), Ribavirin™ virazole (TCN Pharmaceuticals), and DNase (Genentech), as well as other physiologically active therapeutic agents such as antibiotics.

Subjects to be treated by the methods of the present invention include both human and non-human animal (e.g. mouse, rat) subjects, and are preferably mammalian subjects, and most preferably human subjects.

While the invention has been described herein, with respect to certain features, aspects, and embodiments, it will be recognized that the invention may be widely varied, and that numerous other modifications, variations, and other embodiments are possible, and that such modifications, variations, and other embodiments are to be regarded as being within the spirit and scope of the invention.

---

What is claimed is:

1. A method for treating a pulmonary disease state in a warm-blooded animal in need thereof, comprising in vivo delivery by oral or aerosol means to a corporeal situs in the warm-blooded animal of an amount of a non-naturally occurring amphipathic peptide effective for treatment of such disease state, wherein the peptide is selected from the group consisting of SEQ ID Nos. 1–38, wherein the disease state is selected from the group consisting of: cystic fibrosis, neoplasias, bronchogenic cancers, pneumonia, bronchopulmonary viral infections, and bronchopulmonary microbial infections.

2. A method of treating a pulmonary disease state according to claim 1, comprising introduction via aerosol means to a pulmonary locus in the warm-blooded animal in need thereof of an effective amount of the non-naturally occurring synthetic amphipathic peptide effective for treating such disease state, wherein said peptide has a lytic effect for virally infected cells, microbial pathogen cells and neoplastic or transformed cells through peptide interaction with the cellular membrane.

3. A method of treating non-infected, non-neoplastic human cells according to claim 1, comprising delivery of the non-naturally occurring amphipathic peptide wherein said peptide does not have a lytic effect for such cells.

4. A method of treating virally-infected or neoplastic cells according to claim 1, comprising delivery of a non-naturally occurring peptide wherein said peptide has a lytic effect for such cells.

5. A bi-modal method of treating human cystic fibrosis, comprising a concomitant introduction to a pulmonary locus via aerosol means and a gastrointestinal locus via oral means of an amount of a non-naturally occurring amphipathic peptide selected from the group consisting of SEQ ID Nos. 1–38.

6. A method according to claim 5, wherein the non-naturally occurring amphipathic peptide is modified by methylation of lysine residues or glyoxylation of arginine residues to confer enhanced proteolytic digestion resistance to the peptide.

7. A method according to claim 5, wherein the non-naturally occurring amphipathic peptide is methylated on the ε-amino group of lysine residues and the α-amino group of the N-terminal peptide to confer enhanced proteolytic digestion resistance to the peptide.

8. A method according to claim 5, wherein the non-naturally occurring amphipathic peptide is glyoxylated on side chain groups of arginine residues and the α-amino group of the N-terminal peptide to confer enhanced proteolytic digestion resistance to the peptide.

9. A method of treating bronchopulmonary microbial infection in a warm-blooded animal, in need thereof comprising introduction to a pulmonary locus in the warm-blooded animal via aerosol means of a non-naturally occurring amphipathic lytic peptide selected from the group comprising SEQ ID Nos. 1–38 in an amount that is effective in vivo for treating a bronchopulmonary microbial infection by peptide interaction with the cell membrane of microbial pathogens causing said infection.

10. A method according to claim 9, wherein said microbial infection comprises infection by *Pseudomonas aeruginosa*.

11. A method according to claim 9, wherein said microbial infection comprises infection by *Pseudomonas cepacia*.

12. A method according to claim 9, wherein said microbial infection comprises infection by *Mycobacterium tuberculosis*.

13. A method according to claim 9, wherein said microbial infection comprises infection by *Streptococcus pneumoniae*.

14. A method according to claim 9, wherein said microbial infection comprises infection by *Pneumocystis carinii*.

15. A method according to claim 9, wherein said microbial infection comprises infection by *Hemophilus influenzae*.

16. A method according to claim 9, wherein said microbial infection comprises infection by *Klebsiella pneumoniae*.

17. A method according to claim 9, wherein said microbial infection comprises infection by *Chlamydia pneumoniae*.

18. A method of treating human cystic fibrosis according to claim 1, comprising introduction to a pulmonary locus in the warm-blooded animal via aerosol means of an amount of a non-naturally occurring amphipathic peptide effective to treat cystic fibrosis, selected from the group consisting of SEQ ID Nos. 1–38, wherein said peptide has a stimulatory effect on the chloride ion flux of cystic fibrotic defective epithelial cells through peptide interaction with the cell membrane.

19. A method of treating human cystic fibrosis according to claim 1, comprising introduction to a gastrointestinal locus in the warm-blooded animal via oral means of an amount of a non-naturally occurring amphipathic peptide effective to treat cystic fibrosis, selected from the group consisting of SEQ ID Nos. 1–38, wherein said peptide has a stimulatory effect on the chloride ion flux of cystic fibrotic defective epithelial cells through peptide interation with the cell membrane.

20. The method of claim 1 wherein the disease state is selected from the group consisting of cystic fibrosis, pneumonia and a bronchopulmonary microbial infection.

* * * * *

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
  ( A ) LENGTH: 27
  ( B ) TYPE: AMINO ACID
  ( C ) TOPOLOGY: LINEAR ( i i ) MOLECULE TYPE:
  ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 1:

Phe Ala Val Ala Val Lys Ala Val Lys Lys Ala Val Lys Lys Val Lys
1               5                   10                  15

Lys Ala Val Lys Lys Ala Val Lys Lys Lys
            20                  25

( 2 ) INFORMATION FOR SEQ ID NO: 2:

( i ) SEQUENCE CHARACTERISTICS:
  ( A ) LENGTH: 32
  ( B ) TYPE: AMINO ACID
  ( C ) TOPOLOGY: LINEAR ( i i ) MOLECULE TYPE:
  ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 2:

Phe Ala Val Ala Val Lys Ala Val Ala Val Lys Ala Val Lys Lys Ala
1               5                   10                  15

Val Lys Lys Val Lys Lys Ala Val Lys Lys Ala Val Lys Lys Lys Lys
            20                  25                  30

( 2 ) INFORMATION FOR SEQ ID NO: 3:

( i ) SEQUENCE CHARACTERISTICS:
  ( A ) LENGTH: 37
  ( B ) TYPE: AMINO ACID
  ( C ) TOPOLOGY: LINEAR ( i i ) MOLECULE TYPE:
  ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 3:

Phe Ala Val Ala Val Lys Ala Val Ala Val Lys Ala Val Ala Val Lys

```
  1                    5                   10                   15
Ala Val Lys Lys Ala Val Lys Lys Val Lys Lys Ala Val Lys Lys Ala
                20                   25                   30

Val Lys Lys Lys Lys
            35
```

(2) INFORMATION FOR SEQ ID NO: 4:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 4:

```
Phe Ala Val Ala Val Lys Ala Val Lys Lys Ala Val Lys Lys Val Lys
 1               5                   10                   15
Lys Ala Val Lys Lys Ala Val
                20
```

(2) INFORMATION FOR SEQ ID NO: 5:

(i) SEQUENCE CHARACTERISTICS:
        (A) LENGTH: 28
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 5:

```
Phe Ala Val Ala Val Lys Ala Val Ala Val Lys Ala Val Lys Lys Ala
 1               5                   10                   15
Val Lys Lys Val Lys Lys Ala Val Lys Lys Ala Val
                20                   25
```

(2) INFORMATION FOR SEQ ID NO: 6:

(i) SEQUENCE CHARACTERISTICS:
        (A) LENGTH: 33
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 6:

```
Phe Ala Val Ala Val Lys Ala Val Ala Val Lys Ala Val Ala Val Lys
 1               5                  10                 15
Ala Val Lys Lys Ala Val Lys Lys Val Lys Lys Ala Val Lys Lys Ala
            20                  25                 30
Val
```

(2) INFORMATION FOR SEQ ID NO: 7:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 7:

```
Phe Ala Val Gly Leu Arg Ala Ile Lys Arg Ala Leu Lys Lys Leu Arg
 1               5                  10                 15
Arg Gly Val Arg Lys Val Ala Lys Arg Lys Arg
            20                  25
```

(2) INFORMATION FOR SEQ ID NO: 8:

(i) SEQUENCE CHARACTERISTICS:
        (A) LENGTH: 23
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 8:

```
Phe Ala Val Gly Leu Arg Ala Ile Lys Arg Ala Leu Lys Lys Leu Arg
 1               5                  10                 15
Arg Gly Val Arg Lys Val Ala
            20
```

(2) INFORMATION FOR SEQ ID NO: 9:

(i) SEQUENCE CHARACTERISTICS:
        (A) LENGTH: 27

(B) TYPE: AMINO ACID
(C) TOPOLOGY: LINEAR (ii) MOLECULE TYPE:
(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 9:

```
Lys Arg Lys Arg Ala Val Lys Arg Val Gly Arg Arg Leu Lys Lys Leu
 1               5                  10                  15
Ala Arg Lys Ile Ala Arg Leu Gly Val Ala Phe
            20                  25
```

(2) INFORMATION FOR SEQ ID NO: 10:

(i) SEQUENCE CHARACTERISTICS:
(A) LENGTH: 23
(B) TYPE: AMINO ACID
(C) TOPOLOGY: LINEAR (ii) MOLECULE TYPE:
(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 10:

```
Ala Val Lys Arg Val Gly Arg Arg Leu Lys Lys Leu Ala Arg Lys Ile
 1               5                  10                  15
Ala Arg Leu Gly Val Ala Phe
            20
```

(2) INFORMATION FOR SEQ ID NO: 11:

(i) SEQUENCE CHARACTERISTICS:
(A) LENGTH: 30
(B) TYPE: AMINO ACID
(C) TOPOLOGY: LINEAR (ii) MOLECULE TYPE:
(A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 11:

```
Phe Ala Val Gly Leu Arg Ala Ile Lys Arg Ala Leu Lys Lys Leu Arg
 1               5                  10                  15
Arg Gly Val Arg Lys Val Ala Lys Arg Lys Arg Lys Asp Leu
```

(2) INFORMATION FOR SEQ ID NO: 12:

(i) SEQUENCE CHARACTERISTICS:
        (A) LENGTH: 26
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 12:

```
Phe Ala Val Gly Leu Arg Ala Ile Lys Arg Ala Leu Lys Lys Leu Arg
 1               5                  10                  15
Arg Gly Val Arg Lys Val Ala Lys Asp Leu
                20                  25
```

(2) INFORMATION FOR SEQ ID NO: 13:

(i) SEQUENCE CHARACTERISTICS:
        (A) LENGTH: 30
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 13:

```
Lys Arg Lys Arg Ala Val Lys Arg Val Gly Arg Arg Leu Lys Lys Leu
 1               5                  10                  15
Ala Arg Lys Ile Ala Arg Leu Gly Val Ala Phe Lys Asp Leu
                20                  25                  30
```

(2) INFORMATION FOR SEQ ID NO: 14:

(i) SEQUENCE CHARACTERISTICS:
        (A) LENGTH: 26
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED ( x i ) SEQUENCE DESCRIPTION: SEQ ID NO: 14:

Ala Val Lys Arg Val Gly Arg Arg Leu Lys Lys Leu Ala Arg Lys Ile
1               5                   10                  15
Ala Arg Leu Gly Val Ala Phe Lys Asp Leu
            20                  25

( 2 ) INFORMATION FOR SEQ ID NO: 15:

( i ) SEQUENCE CHARACTERISTICS:
            ( A ) LENGTH: 27
            ( B ) TYPE: AMINO ACID
            ( C ) TOPOLOGY: LINEAR ( i i ) MOLECULE TYPE:
            ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 15:

Lys Lys Lys Lys Phe Val Lys Lys Val Ala Lys Lys Val Lys Lys Val
1               5                   10                  15
Ala Lys Lys Val Ala Lys Val Ala Val Ala Val
            20                  25

( 2 ) INFORMATION FOR SEQ ID NO: 16:

( i ) SEQUENCE CHARACTERISTICS:
            ( A ) LENGTH: 32
            ( B ) TYPE: AMINO ACID
            ( C ) TOPOLOGY: LINEAR ( i i ) MOLECULE TYPE:
            ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 16:

Lys Lys Lys Lys Phe Val Lys Lys Val Ala Lys Lys Val Lys Lys Val
1               5                   10                  15
Ala Lys Lys Val Ala Lys Val Ala Val Ala Lys Val Ala Val Ala Val
            20                  25                  30

( 2 ) INFORMATION FOR SEQ ID NO: 17:

( i ) SEQUENCE CHARACTERISTICS:
            ( A ) LENGTH: 37
            ( B ) TYPE: AMINO ACID
            ( C ) TOPOLOGY: LINEAR ( i i ) MOLECULE TYPE:
            ( A ) DESCRIPTION: PEPTIDE ( i i i ) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 17:

Lys Lys Lys Lys Phe Val Lys Lys Val Ala Lys Lys Val Lys Val
1               5                   10                  15
Ala Lys Lys Val Ala Lys Val Ala Val Ala Lys Val Ala Val Ala Lys
                20                  25                  30
Val Ala Val Ala Val
            35

(2) INFORMATION FOR SEQ ID NO: 18:

(i) SEQUENCE CHARACTERISTICS:
    (A) LENGTH: 23
    (B) TYPE: AMINO ACID
    (C) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 18:

Phe Val Lys Lys Val Ala Lys Lys Val Lys Lys Val Ala Lys Lys Val
1               5                   10                  15
Ala Lys Val Ala Val Ala Val
                20

(2) INFORMATION FOR SEQ ID NO: 19:

(i) SEQUENCE CHARACTERISTICS:
    (A) LENGTH: 28
    (B) TYPE: AMINO ACID
    (C) TOPOLOGY: LINEAR (ii) MOLECULE TYPE:
    (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 19:

Phe Val Lys Lys Val Ala Lys Lys Val Lys Lys Val Ala Lys Lys Val
1               5                   10                  15
Ala Lys Val Ala Val Ala Lys Val Ala Val Ala Val
                20                  25

(2) INFORMATION FOR SEQ ID NO: 20:

-continued ( i ) SEQUENCE CHARACTERISTICS:
  ( A ) LENGTH: 33
  ( B ) TYPE: AMINO ACID
  ( C ) TOPOLOGY: LINEAR ( i i ) MOLECULE TYPE:
  ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 20:

```
Phe Val Lys Lys Val Ala Lys Lys Val Lys Lys Val Ala Lys Lys Val
 1               5                  10                 15
Ala Lys Val Ala Val Ala Lys Val Ala Val Ala Lys Val Ala Val Ala
                20                  25                 30
Val
```

( 2 ) INFORMATION FOR SEQ ID NO: 21:

( i ) SEQUENCE CHARACTERISTICS:
  ( A ) LENGTH: 27
  ( B ) TYPE: AMINO ACID
  ( C ) TOPOLOGY: LINEAR ( i i ) MOLECULE TYPE:
  ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 21:

```
Lys Lys Lys Lys Phe Val Lys Lys Val Ala Lys Val Ala Lys Lys Val
 1               5                  10                 15
Ala Lys Val Ala Lys Lys Val Ala Lys Lys Val
                20                  25
```

( 2 ) INFORMATION FOR SEQ ID NO: 22:

( i ) SEQUENCE CHARACTERISTICS:
  ( A ) LENGTH: 32
  ( B ) TYPE: AMINO ACID
  ( C ) TOPOLOGY: LINEAR ( i i ) MOLECULE TYPE:
  ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 22:

```
Lys Lys Lys Lys Phe Val Lys Lys Val Ala Lys Val Ala Lys Lys Val
 1           5                   10              15
Ala Lys Val Ala Lys Lys Val Ala Lys Val Ala Lys Lys Val Ala
         20              25              30
```

( 2 ) INFORMATION FOR SEQ ID NO: 23:

( i ) SEQUENCE CHARACTERISTICS:
        ( A ) LENGTH: 37
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 23:

```
Lys Lys Lys Lys Phe Val Lys Lys Val Ala Lys Val Ala Lys Lys Val
 1           5                   10              15
Ala Lys Val Ala Lys Lys Val Ala Lys Val Ala Lys Lys Val Ala
         20              25              30
Lys Val Ala Lys Lys
         35
```

( 2 ) INFORMATION FOR SEQ ID NO: 24:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 24:

```
Phe Val Lys Lys Val Ala Lys Val Ala Lys Lys Val Ala Lys Val Ala
 1           5                   10              15
Lys Lys Val Ala Lys Lys Val
         20
```

( 2 ) INFORMATION FOR SEQ ID NO: 25:

( i ) SEQUENCE CHARACTERISTICS:
        ( A ) LENGTH: 28
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 25:

```
Phe Val Lys Lys Val Ala Lys Val Ala Lys Lys Val Ala Lys Val Ala
 1               5                  10                 15
Lys Lys Val Ala Lys Lys Val Ala Lys Lys Val Ala
            20                  25
```

( 2 ) INFORMATION FOR SEQ ID NO: 26:

( i ) SEQUENCE CHARACTERISTICS:
( A ) LENGTH: 33
( B ) TYPE: AMINO ACID
( C ) TOPOLOGY: LINEAR ( i i ) MOLECULE TYPE:
( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 26:

```
Phe Val Lys Lys Val Ala Lys Val Ala Lys Lys Val Ala Lys Val Ala
 1               5                  10                 15
Lys Lys Val Ala Lys Lys Val Ala Lys Lys Val Ala Lys Val Ala Lys
            20                  25                 30
Lys
```

( 2 ) INFORMATION FOR SEQ ID NO: 27:

( i ) SEQUENCE CHARACTERISTICS:
( A ) LENGTH: 27
( B ) TYPE: AMINO ACID
( C ) TOPOLOGY: LINEAR ( i i ) MOLECULE TYPE:
( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 27:

```
Phe Val Lys Lys Val Ala Lys Val Ala Lys Lys Val Ala Lys Val Ala
 1               5                  10                 15
Lys Lys Val Ala Lys Lys Val Lys Lys Lys Lys
            20                  25
```

( 2 ) INFORMATION FOR SEQ ID NO: 28:

( i ) SEQUENCE CHARACTERISTICS:

( A ) LENGTH: 32
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 28:

```
Phe Val Lys Lys Val Ala Lys Val Ala Lys Lys Val Ala Lys Val Ala
 1               5                  10                  15
Lys Lys Val Ala Lys Lys Val Ala Lys Lys Val Ala Lys Lys Lys Lys
             20                  25                  30
```

( 2 ) INFORMATION FOR SEQ ID NO: 29:

( i ) SEQUENCE CHARACTERISTICS:
        ( A ) LENGTH: 37
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 29:

```
Phe Val Lys Lys Val Ala Lys Val Ala Lys Lys Val Ala Lys Val Ala
 1               5                  10                  15
Lys Lys Val Ala Lys Lys Val Ala Lys Lys Val Ala Lys Val Ala Lys
             20                  25                  30
Lys Lys Lys Lys Lys
         35
```

( 2 ) INFORMATION FOR SEQ ID NO: 30:

( i ) SEQUENCE CHARACTERISTICS:
        ( A ) LENGTH: 16
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 30:

```
Phe Lys Val Lys Ala Lys Val Lys Ala Lys Val Lys Lys Lys Lys
  1               5                  10                 15
```

(2) INFORMATION FOR SEQ ID NO: 31:

(i) SEQUENCE CHARACTERISTICS:
        (A) LENGTH: 21
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 31:

```
Phe Lys Val Lys Ala Lys Val Lys Ala Lys Val Lys Ala Lys Val Lys
  1               5                  10                 15
Ala Lys Lys Lys Lys
         20
```

(2) INFORMATION FOR SEQ ID NO: 32:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 32:

```
Phe Lys Val Lys Ala Lys Val Lys Ala Lys Val Lys Ala Lys Val Lys
  1               5                  10                 15
Ala Lys Val Lys Ala Lys Val Lys Lys Lys Lys
         20                  25
```

(2) INFORMATION FOR SEQ ID NO: 33:

(i) SEQUENCE CHARACTERISTICS:
        (A) LENGTH: 12
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 33:

```
Phe Lys Val Lys Ala Lys Val Lys Ala Lys Val Lys
1               5                   10
```

( 2 ) INFORMATION FOR SEQ ID NO: 34:

( i ) SEQUENCE CHARACTERISTICS:
        ( A ) LENGTH: 17
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 34:

```
Phe Lys Val Lys Ala Lys Val Lys Ala Lys Val Lys Ala Lys Val Lys
1               5                   10                  15
Ala
```

( 2 ) INFORMATION FOR SEQ ID NO: 35:

( i ) SEQUENCE CHARACTERISTICS:
        ( A ) LENGTH: 23
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC ( v i i ) IMMEDIATE SOURCE: SYNTHETIC ( x ) PUBLICATION INFORMATION: NOT PREVIOUSLY PUBLISHED ( x i ) SEQUENCE DESCRIPTION: SEQ ID NO: 35:

```
Phe Lys Val Lys Ala Lys Val Lys Ala Lys Val Lys Ala Lys Val Lys
1               5                   10                  15
Ala Lys Val Lys Ala Lys Val
                20
```

( 2 ) INFORMATION FOR SEQ ID NO: 36:

( i ) SEQUENCE CHARACTERISTICS:
        ( A ) LENGTH: 16
        ( B ) TYPE: AMINO ACID
        ( C ) TOPOLOGY: LINEAR ( i i ) MOLECULE TYPE:
        ( A ) DESCRIPTION: PEPTIDE ( i i i ) HYPOTHETICAL: NO ( v ) FRAGMENT TYPE: COMPLETE PEPTIDE ( v i ) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 36:

```
Lys Lys Lys Lys Phe Lys Val Lys Ala Lys Val Lys Ala Lys Val Lys
 1               5                   10                  15
```

(2) INFORMATION FOR SEQ ID NO: 37:

(i) SEQUENCE CHARACTERISTICS:
        (A) LENGTH: 21
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 37:

```
Lys Lys Lys Lys Phe Lys Val Lys Ala Lys Val Lys Ala Lys Val Lys
 1               5                   10                  15
Ala Lys Val Lys Ala
             20
```

(2) INFORMATION FOR SEQ ID NO: 38:

(i) SEQUENCE CHARACTERISTICS:
        (A) LENGTH: 27
        (B) TYPE: AMINO ACID
        (C) TOPOLOGY: LINEAR (ii) MOLECULE TYPE:
        (A) DESCRIPTION: PEPTIDE (iii) HYPOTHETICAL: NO (v) FRAGMENT TYPE: COMPLETE PEPTIDE (vi) ORIGINAL SOURCE: SYNTHETIC (vii) IMMEDIATE SOURCE: SYNTHETIC (x) PUBLICATION INFORMATION: NOT PREVIOUSLY PUBLISHED (xi) SEQUENCE DESCRIPTION: SEQ ID NO: 38:

```
Lys Lys Lys Lys Phe Lys Val Lys Ala Lys Val Lys Ala Lys Val Lys
 1               5                   10                  15
Ala Lys Val Lys Ala Lys Val Lys Ala Lys Val
             20                  25
```